United States Patent [19]

Amano et al.

[11] Patent Number: 4,889,797

[45] Date of Patent: Dec. 26, 1989

[54] DRY ANALYTICAL ELEMENT HAVING A SPREAD CONTROL AREA FOR ASSAYING ENZYME ACTIVITY

[75] Inventors: Yoshikazu Amano; Shigeki Kageyama; Harumi Katsuyama, all of Saitama, Japan

[73] Assignee: Fuji Photo Film Co., Ltd., Kanagawa, Japan

[21] Appl. No.: 54,432

[22] Filed: May 26, 1987

[30] Foreign Application Priority Data

May 28, 1986 [JP] Japan ................................ 61-122875
May 28, 1986 [JP] Japan ................................ 61-122876
Jun. 19, 1986 [JP] Japan ................................ 61-143754

[51] Int. Cl.$^4$ .................... C12Q 1/00; C12Q 1/48; G01N 33/50; G01N 30/90

[52] U.S. Cl. ........................................ 435/4; 435/291; 435/805; 435/810; 422/56; 422/57; 422/58; 422/60; 422/61; 422/68; 436/808; 436/810

[58] Field of Search ............... 435/4, 805, 7, 291, 435/810; 436/810, 808; 422/56, 57, 68, 58, 60, 61; 106/901

[56] References Cited

U.S. PATENT DOCUMENTS

| | | | |
|---|---|---|---|
| 3,867,258 | 2/1975 | Forgione | 435/26 X |
| 3,992,158 | 11/1976 | Przybylowicz et al. | 422/57 X |
| 4,258,001 | 3/1981 | Pierce et al. | 435/805 X |
| 4,275,031 | 6/1981 | Fischer et al. | 422/57 |
| 4,486,537 | 12/1984 | Koyama et al. | 422/57 X |
| 4,615,983 | 10/1986 | Koyama et al. | 422/56 X |

FOREIGN PATENT DOCUMENTS

| | | | |
|---|---|---|---|
| 0162302 | 11/1985 | European Pat. Off. | 422/56 |
| 0254457 | 1/1988 | European Pat. Off. | 422/56 |

OTHER PUBLICATIONS

D'Souza et al, "Multilaboratory Evaluation of Six Enzyme Tests on the Kodak Ektachem 700 Analyzer", (poster session XII International Congress of Clinical Chemistry), 1984.

*Primary Examiner*—Robert J. Warden
*Assistant Examiner*—Carol A. Spiegel
*Attorney, Agent, or Firm*—Jules E. Goldberg

[57] ABSTRACT

A dry analytical element for assaying an enzyme in a liquid is disclosed, comprising a support having provided thereon at least a porous liquid-spreading layer composed of water non-absorbent fibers, wherein said porous liquid-spreading layer contains a substrate for an enzyme to be assayed and a hydrophilic polymer in an amount effective to decrease a spreading area by at least 20%. The analytical element exhibits high sensitivity and high reproducibility.

11 Claims, No Drawings

DRY ANALYTICAL ELEMENT HAVING A SPREAD CONTROL AREA FOR ASSAYING ENZYME ACTIVITY

BACKGROUND OF THE INVENTION

1. Field of the Invention

This invention relates to a dry analytical element suitable for assaying enzymatic activity in a liquid.

2. Description of the Prior Art

Dry analytical elements, especially integral multilayer dry analytical elements are known and described e.g., in U.S. Pat. No. 3,992,158 and Japanese Patent Application (OPI) No. 1643/81 (The term "OPI" as used herein means "unexamined published application"). It is disclosed in Analytical Chemistry, Vol. 55, No. 4, 498A-514A (1983) that the integral multilayer dry analytical element can be applied to the assay of enzymes in serum.

The integral multilayer dry analytical element generally comprises a liquid-spreading layer having a liquid measuring function as an uppermost layer. When a liquid of an amount V is developed in the liquid spreading layer, the developed area is proportional to V (V=ka). Since the amount of the liquid per unit area is decided by the proportionality constant k between the spreading area and the liquid amount V, the analytical sensitivity depends on the proportionality constant k. As the proportionality constant k becomes smaller, the amount of the liquid per unit area becomes greater so that the enzymatic activity per unit area becomes higher and the analytical sensitivity is increased.

An integral multilayer dry analytical element in which the porous liquid-spreading layer comprises water non-absorbent fibers is disclosed in Japanese Patent Application (OPI) Nos. 164356/80 and 222769/85. Water non-absorbent long fibers, such as polyesters, polyamides (e.g., nylon), etc., retain little water and, when woven or knitted, provide a uniform spreading layer and are, therefore, suitable for use in dry analytical elements utilizing a reaction rate method. However, such a porous liquid-spreading layer composed of water non-absorbent fibers has a large proportionality constant k so that a high analytical sensitivity cannot be assured.

SUMMARY OF THE INVENTION

One object of this invention is to provide an integral multilayer dry analytical element for assaying enzymatic activities using a reaction rate method, which shows high sensitivity, and preferably high sensitivity combined with high reproducibility.

It has now been found that the above object can be accomplished by a dry analytical element for assaying enzymes in a liquid, which comprises at least a porous liquid-spreading layer composed of water non-absorbent fibers, wherein said porous liquid-spreading layer contains a substrate for an enzyme to be assayed and a water-soluble polymer in an amount sufficient to decrease the spreading area by at least 20%.

DESCRIPTION OF THE PREFERRED EMBODIMENT

In a preferred embodiment of this invention, the above-described polymer is a hydrophilic polymer selected from the group consisting of a homo- or copolymer comprising a monomer unit represented by formula (I) or (II) shown below, a copolymer comprising said monomer unit and another copolymerizable monomer unit, and a cellulose derivative.

Formula (I) is represented by

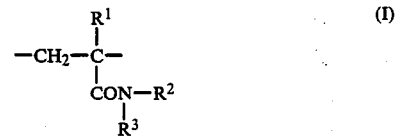

wherein $R^1$ represents a hydrogen atom or a lower alkyl group; and $R^2$ and $R^3$ each represents a hydrogen atom, a substituted or unsubstituted aliphatic hydrocarbon residue; a substituted or unsubstituted aromatic hydrocarbon residue, or a substituted or unsubstitued heterocyclic group, or $R^2$ and $R^3$ are taken together to form a ring.

wherein $R^4$ has the same meaning as $R^1$; and Q represents

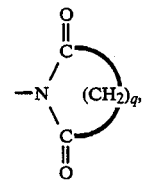

wherein q represents an integer of from 2 to 4, $-NR^5-CO-R^6$, wherein $R^5$ represents an alkyl group having from 1 to 4 carbon atoms; and $R^6$ represents a hydrogen atom or an alkyl group having from 1 to 4 carbon atoms, or

wherein $Z^1$ represents an atomic group forming a lactam ring, an oxazolidone ring or a pyridone ring.

In formula (I), the lower alkyl group as represented by $R^1$ preferably contains from 1 to 4 carbon atoms and more preferably represents a hydrogen atom or a methyl group.

The aliphatic hydrocarbon residue as represented by $R^2$ or $R^3$ preferably includes an alkyl or cycloalkyl group having from 1 to 4 carbon atoms. The aliphatic hydrocarbon residue may be substituted with an aryl group, e.g., a phenyl group, a hydroxyl group, an alkoxy group having from 1 to 4 carbon atoms, e.g., a methoxy group, a halogen atom, e.g., a chlorine atom, an alkylamino or dialkylamino group having from 1 to 4 carbon atoms in the alkyl moiety thereof, e.g., a dimethylamino group, and the like. The aromatic hydrocarbon residue for $R^2$ or $R^3$ preferably contains from 6 to 7 carbon atoms. The aromatic hydrocarbon residue may be substituted with an alkyl group having from 1 to 4 carbon atoms, e.g., a methyl group, a hydroxyl group, an alkoxy group having from 1 to 4 carbon atoms, e.g., a methoxy group, a halogen atom, e.g., a chlorine atom, an alkylamino or dialkylamino group having from 1 to 4 carbon atoms in the alkyl moiety thereof, e.g., a dimethylamino group, and the like. The heterocyclic group for $R^2$ or $R^3$ includes a 5- or 6-membered ring containing at least one of nitrogen, oxygen and sulfur atoms. Specific examples of preferred groups for $R^2$ or $R^3$ are a hydrogen atom, a methyl group, an ethyl group, a benzyl group, a hydroxyethyl group, a cyclohexyl group, a phenyl group, a piperidino group, and a morpholino group.

The total number of carbon atoms contained in $R^2$ and $R^3$ is preferably up to 12, and more preferably up to 6.

The polymer comprising the repeating unit represented by formula (I) includes a homopolymer of the repeating unit of formula (I), a copolymer comprising at least two different repeating units of formula (I), and a copolymer comprising at least one repeating unit of formula (I) and another monomer unit derived from an addition polymerizable unsaturated compound.

Specific examples of the monomers providing the repeating unit of formula (I) include acrylamide, N-methylacrylamide, N-ethylacrylamide, N-(n-propyl)acrylamide, N-isopropylacrylamide, N-(n-butyl)acrylamide, N-(t-butyl)acrylamide, N-(n-octyl)acrylamide, N-(isoamyl)acrylamide, N-(t-octyl)acrylamide, N-laurylacrylamide, N-cyclohexylacrylamide, N-benzylacrylamide, N-(β-dimethylaminoethyl)acrylamide, N-phenylacrylamide, N-(1,1-dimethyl-3-hydroxybutylacrylamide), N,N-dimethylmethacrylamide, N,N-diethylacrylamide, N,N-dioctylacrylamide, N-(1,1-dimethyl-3-oxobutyl)acrylamide, N-acryloylmorpholine, N-methyl-N'-acryloylpiperazine, N-ethyl-N'-acryloylpiperazine, N-acryloylpiperidine, N-(β-morpholinoethyl)acrylamide, N-(3,5-dimethylmorpholinoethyl)acrylamide, methacrylamide, N-methylmethacrylamide, N-ethylmethacrylamide, N-(t-butyl)methacrylamide, N-(t-octyl)methacrylamide, N-benzylmethacrylamide, N-cyclohexylmethacrylamide, N-phenylmethacrylamide, N,N-dimethylmethacrylamide, N,N-diethylmethacrylamide, N,N-dipropylmethacrylamide, N-methyl-N-phenylmethacrylamide, N-methacryloyl-N'-methylpiperazine, N-methacryloylpiperidine, 4-methacryloyl-2,6-dimethylmorpholine, N-methacryloyl-N'-ethylpiperazine, etc.

The addition polymerizable unsaturated compounds from another monomer unit can be derived and which can be copolymerized with the monomer having the repeating unit of formula (I) include acrylic acid, methacrylic acid, maleic acid, fumaric acid, itaconic acid, crotonic acid, acrylic esters (e.g., methyl acrylate, ethyl acrylate, n-propyl acrylate, isopropyl acrylate, n-butyl acrylate, octyl acrylate, 2-chloroethyl acrylate, 2-cyanoethyl acrylate, N-(β-dimethylaminoethyl) acrylate, benzyl acrylate, cyclohexyl acrylate, phenyl acrylate, etc.), methacrylic esters (e.g., methyl methacrylate, ethyl methacrylate, n-propyl methacrylate, isopropyl methacrylate, n-butyl methacrylate, octyl methacrylate, cyclohexyl methacrylate, benzyl methacrylate, 3-sulfopropyl methacrylate, etc.), allyl compounds (e.g., allyl butyl ether, allyl phenyl ether, etc.), vinyl ethers (e.g., methyl vinyl ether, butyl vinyl ether, octyl vinyl ether, methoxyethyl vinyl ether, 2-chloroethyl vinyl ether, 2-hydroxyethyl vinyl ether, (2-dimethylaminoethyl) vinyl ether, vinyl phenyl ether, vinyl tollyl ether, vinyl chlorophenyl ether, etc.), p-vinylbenzoic acid, vinyl esters (e.g., methyl p-vinylbenzoate, etc.), vinyl heterocyclic compounds (e.g., vinylpyridine, N-vinylimidazole, N-vinylcarbazole, N-vinylpyrrolidone, N-vinyloxazolidone, etc.), methyl vinyl ketone, phenyl vinyl ketone, styrene or derivatives thereof (e.g., chloromethylstyrene, p-methylstyrene, etc.), maleic esters (e.g., ethyl maleate, butyl maleate, dibutyl maleate, octyl maleate, etc.), fumaric esters (e.g., ethyl fumarate, dibutyl fumarate, octyl fumarate, etc.), itaconic esters (e.g., methyl itaconate, ethyl itaconate, diethyl itaconate, etc., crotonamide, crotonic esters (e.g., butyl crotonate, glycerin monocrotonate, etc.), methyl sorbate, olefins (e.g., ethylene, propylene, 1-butene, dicyclopentadiene, 4-methyl-1-hexene, 4,4-dimethyl-1-pentene, etc.), halogenated olefins (e.g., vinyl chloride, vinylidene chloride, isoprene, etc.), unsaturated nitriles (e.g., acrylonitrile, methacrylonitrile, etc.), and the like. These comonomers may be used either individually or in combinations of two or more thereof. These comonomers may be used either individually or in combinations of two or more thereof.

In formula II, when Q is —NR$^5$—CO—R$^6$ R$^5$ may be an alkyl group having from 1 to 4 carbon atoms, and, preferably, a methyl group or an ethyl group. R$^6$ represents a hydrogen atom or an alkyl group having from 1 to 4 carbon atoms, and, preferably, a hydrogen atom, a methyl group or an ethyl group.

Preferred among the repeating units of formula (II) are those wherein $R^4$ is a hydrogen atom; and Q represents:

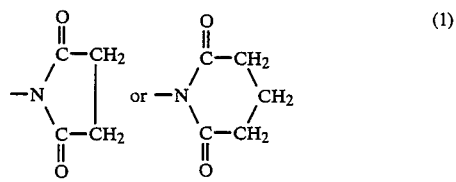

wherein $R^5$ represents a methyl group or an ethyl group; and $R^6$ represents a hydrogen atom, a methyl group or an ethyl group, or

wherein $Z^1$ represents an atomic group forming a 5- or 6-membered lactam ring, or oxazolidone ring.

The most preferred among them is a repeating unit wherein Q represents a pyrrolidone residual group or an oxazolidone residual group.

The polymer having the repeating unit of formula (II) may be a homopolymer or a copolymer comprising at least two repeating units of formula (II) or a copolymer comprising at least one repeating unit of formula (I) and another repeating unit derived from addition polymerizable unsaturated compounds.

Monomers providing the repeating unit of formula (II) are represented by formula (III)

wherein R⁴ and Q are as defined above.

Specific examples of the monomers represented by formula (III) are vinyl acetate, N-vinylsuccinimide, N-vinylglutaramide, N-vinyladipimide, N-methyl-N-methyl-N-vinylformamide, N-methyl-N-vinylacetamide, N-ethyl-N-vinylacetamide, N-methy-N-vinylpropionamide, N-vinylpyrrolidone, N-vinylpiperidone, N-vinyl-ε-caprolactam, N-vinyloxazolidone, N-vinylmorpholine, N-vinyl-2-pyridone, etc. Preferred of these are vinyl acetate, N-vinylsuccinimide, N-vinylglutarmide, N-methyl-N-vinylacetamide, N-ethyl-N-vinylacetamide, N-vinylpyrrolidone N-vinylpiperidone, and N-vinyloxazolidone. The most preferred monomer among them is N-vinylpyrrolidone.

The addition polymerizable unsaturated compounds copolymerizable with the monomer of formula (III) include the monomers providing the repeating unit of formula (I) and the monomers copolymerizable therewith, preferably include acrylic acid, methacrylic acid, maleic anhydride, acrylamide, N-methylacrylamide, N,N-dimethylacrylamide, N-ethylacrylamide, N-(β-hydroxyethyl)acrylamide, methacrylamide, N-methylmethacrylamide, and the like. From the standpoint of the hydrophilic properties of the produced polymer, preferred among these comonomers are acrylic acid, methacrylic acid, 2-hydroxyethyl acrylate, 2-methoxyethyl acrylate, sulfopropyl acrylate, acrylamide, dimethylacrylamide, 2-acryloylamino-2-methylpropanesulfonic acid, hydroxyethylacrylamide, methacrylamide, methyl vinyl ether, sodium styrenesulfonate, N-vinyl-3,5-dimethyltriazole, and maleic anhydride.

The copolymerization ratio of the copolymer having the repeating unit of formula(I) or (II) is not particularly limited, but the content of the repeating unit of formula (I) or (II) in the copolymer preferably ranges from 20 to 100 mol %, and more preferably from 50 to 100 mol %.

The polymer having a repeating unit of formula (I) or (II) can be synthesized by the processes disclosed in British Pat. Nos. 1,211,039 and 961,395, Japanese Patent Publication No. 29195/72, Japanese Patent Application (OPI) Nos. 76593/73, 92022/73, 21134/75, and 120634/75, U.S. Pat. Nos. 2,681,897, 3,227,672, 3,290,417, 3,262,919, 3,245,932, and 3,230,275, John C. Petropoulosu et al., *Official Digest*, Vol. 33, 719–736 (1961), Shunsuke Murahashi, et al. (ed.), *Gosei Kobunshi*, Vol. 1, 246–290, ibid, Vol. 3, 1–108, etc. The polymerization is generally carried out at a temperature of from 20° to 180° C., and, preferably, from 40° to 120° C., using from 0.05 to 5% by weight of a radical polymerization initiator based on the monomers. The initiators to be used include azobis compounds, peroxides, hydroperoxides, redox catalysts, such as, potassium persulfate, t-butyl peroctoate, benzoyl peroxide, azobisisobutylonitrile, etc.

Typical examples of the polymer having the repeating unit of formula (I) are:
(1) poly(N-ethylacrylamide),
(2) polyacrylamide,
(3) poly(N,N-dimethylacrylamide),
(4) polymethacrylamide,
(5) acrylamide/ethyl acrylate copolymer (40:60 by mol),
(6) N,N-dimethylacrylamide/methyl acrylate copolymer (50:50 by mol),
(7) acrylamide/butyl acrylate copolymer (60:40 by mol),
(8) N-acrylamide/ethyl acrylate copolymer (50:50 by mol),
(9) N,N-dimethylacrylamide/maleic acid copolymer (70:30 by mol),
(10) acrylamide/ethyl acrylate copolymer (40:60 by mol),
(11) acrylamide/ethyl acrylate (50:50 by mol),
(12) N-methyl acrylamide/ethyl acrylate copolymer (50:50 by mol),
(13) N-ethylacrylamide/acrylic acid copolymer (30:70 by mol),
(14) N-methyl methacrylamide/ethyl acrylate copolymer (50:50 by mol),
(15) N,N-dimethylmethacrylamide/propyl acrylate copolymer (35:65 by mol),
(16) N-acryloylmorpholine/ethyl acrylate copolymer (40:60 by mol),
(17) poly[N-(3-dimethylaminopropyl)acrylamide], and
(18) poly(N-methacryloylpiperazine).

Typical examples of the polymer containing the repeating unit of formula (II) are:-
(19) poly(N-vinylpyrrolidone),
(20) poly(N-vinyloxazolidone),
(21) poly(N-vinylsuccinimide),
(22) poly(N-vinylglutarimide),
(23) poly(N-vinylpiperidone),
(24) poly(N-vinyl-ε-caprolactam),
(25) poly(N-methyl-N-vinylacetamide),
(26) poly(N-ethyl-N-vinylacetamide),
(27) vinyl alcohol/N-vinylpyrrolidone copolymer (30:70 by mol),
(28) N-vinylpyrrolidone/vinyl acetate copolymer (70:30 by mol),
(29) N-vinylpyrrolidone/2-hydroxyethyl acrylate copolymer (80:20 by mol),
(30) N-vinylpyrrolidone/acrylic acid copolymer (90:10 by mol),
(31) N-vinylpiperidone/2-methoxyethyl acrylate copolymer (70:30 by mol),
(32) N-vinylpiperidone/methyl vinyl ether copolymer (90:10 by mol),
(33) N-vinyloxazolidone/vinyl alcohol copolymer (65:35 by mol),
(34) N-vinyloxazolidone/acrylic acid copolymer (80:20 by mol),
(35) N-vinylpyrrolidone/N-vinylpiperidone/hydroxyethyl acrylate copolymer (40:30:30 by mol),
(36) vinyl alcohol/vinyl acetate/N-vinyl-2-pyridone copolymer (70:25:5 by mol),
(37) N-vinylpyrrolidone/2-hydroxyethyl acrylate/vinyl acetate copolymer (70:20:10), and
(38) N-vinylpyrrolidone/vinyl alcohol/vinyl propionate/sodium styrenesulfonate copolymer (40:40:5:15 by mol).

Specific examples of the copolymers having the repeating unit of (II) and other addition polymerizable unsaturated comonomers are:-
(39) N-vinylpyrrolidone/acrylamide copolymer (60:40 by mol),
(40) N-vinylpyrrolidone/2-acryloylamino-2-methylpropanesulfonic acid copolymer (75:25 by mol),
(41) N-vinylpyrrolidone/2-methacrylamide copolymer (60:40 by mol),
(42) N-vinyloxazolidone/N-(2-hydroxyethyl)acrylamide copolymer (60:40 by mol),
(43) N-vinyloxazolidone/N-(2-hydroxyethyl)acrylamide copolymer (70:30 by mol),
(44) N-vinylpyrrolidone/N-vinylmorpholine/acrylamide copolymer (50:20:30 by mol),

(45) N-vinylsuccinimide/N-vinyl-ε-caprolactam/acrylamide copolymer (40:20:40 by mol),
(46) N-vinyloxazolidone/acrylamide/acrylic acid copolymer (60:20:20 by mol),
(47) N-vinylpyrrolidone/acrylamide/vinyl acetate/acrylic acid copolymer (60:20:10:10 by mol), and
(48) N-vinylpyrrolidone/dimethylacrylamide copolymer (70:30 by mol).

The polymers having the repeating unit represented by formula (I) or (II) usually have a molecular weight of 2,000 or more, and preferably from 8,000 to 700,000.

Any of the polymers having the repeating unit represented by formula (I) or (II) has relatively high hydrophilic properties. Incorporation of these polymers into the porous spreading layer can be carried out by dissolving the polymer in water or a water-miscible organic solvent, applying the aqueous or organic solvent solution to a spreading layer by coating or dipping, and drying. The organic solvent which can be used includes methyl acetate, "ethyl acetate, butyl acetate, methyl isobutyl ketone, β-ethoxyethyl acetate, methylcarbitol, dioxane, cyclohexane, cyclohexanone, dipropylene glycol, N,N-dimethylformamide, propanol, isopropanol, methanol, butanol, sec-butanol, ethylene glycol monomethyl ether, ethylene glycol monobutyl ether, and the like.

These polymers are added to a spreading layer in an amount effective to decrease a spreading area by at least 20%. Such an amount preferably ranges from 2 to 15 g/m².

The cellulose derivative which can be used in the present invention preferably includes a hydroxyalkyl cellulose having from 1 to 3 carbon atoms in the alkyl moiety thereof, (e.g., hydroxypropyl cellulose), a cellulose mixed alkyl ether (e.g., hydroxypropyl-methylcellulose), and the like.

The aforesaid cellulose derivative is added to a spreading layer in an amount effective to decrease a spreading area by at least 20%. Such an amount preferably ranges from 0.5 to 15 g/m², and more preferably from 0.7 to 10 g/m².

The substrate for an enzyme is one receiving any action of the specific enzyme, for example, alanine for alanine aminotransferase; aspartate for aspartate aminotransferase; γ-glutamyl-p-nitroanilide for γ-glutamyl transferase; lactate for lactate dehydrogenase; pyrophosphate (ATP, ADP), monophosphate and p-nitrophenylphosphates for alkaline phosphotase; starch for L-amylase, etc.

The present invention can be applied to a wide variety of known dry analytical elements, and particularly to elements containing a solid carrier permeable to both a detecting reagent system and a liquid to be analyzed. The elements generally comprise a support, a detecting layer and/or a reactive reagent layer, and a porous liquid-spreading layer. The elements may further contain a reflective layer, an adhesive layer, a filter layer, a water-absorbent layer, a subbing layer and any other known layers. Examples of such analytical elements are disclosed in U.S. Pat. Nos. 3,992,158 and 4,042,335 and Japanese Patent Applciation (OPI) No. 164356/80.

In the cases where a dry analytical element of the present invention contains a support, practical embodiments of such an element include (1) a structure comprising a support having provided thereon a detecting layer and further provided thereon a liquid-spreading layer, (2) a structure comprising a support having provided thereon a reactive reagent layer and further provided thereon a liquid-spreading layer (3) a structure comprising a support having provided thereon a detecting layer, a reactive reagent layer, and a liquid-spreading layer in this order, and (4) a structure comprising a support having provided thereon a detecting layer, a second reactive reagent layer, a first reactive reagent layer, and a liquid-spreading layer in this order.

In the structures (1) to (4), a light-shielding layer and/or a filter layer may be provided between the detecting layer and the reactive reagent layer or the liquid-spreading layer, between the reactive reagent layer and the liquid-spreading layer, or between the second reactive reagent layer and the first reactive reagent layer.

In the present invention, the hydrophilic polymer selected from the group consisting of the polymers containing the repeating unit of formula (I) or (II) and the cellulose derivatives may be incorporated into not only a liquid-spreading layer. but also other layers, e.g., a reagent layer.

It is preferable that each of the aforesaid layers and a water-absorbent layer be provided on a support permeable to light but impermeable to water via, if necessary, a subbing layer, etc.

The water-absorbent layer is a layer which is permeable to water but substantially impermeable to the substance to be finally detected. This layer is provided, preferably between a support and a detecting layer or a reagent layer, in cases where the substance to be finally detected is a sparingly diffusible high polymeric substance. Such a water-absorbent layer preferably comprises a film-forming hydrophilic polymer which is swollen with absorbed water.

The detecting layer is a layer which is substantially permeable to a substance to be finally detected and contains no reactive reagent. This layer comprises a hydrophilic polymer as a main component and, if desired, a surface active agent (cationic, amphoteric or nonionic), a hardener, a buffer agent, etc.

The hydrophilic polymer which can be used for the water-absorbent layer or detecting layer is a natural or synthetic hydrophilic polymer usually having a degree of swelling of from about 1.5 to about 20, and preferably, from about 2.5 to about 15, when absorbing water. Examples of such a hydrophilic polymer include gelatin (e.g., acid-processed gelatin, deionized gelatin, etc.), a gelatin derivative (e.g., a phthalated gelatin, etc.), agarose, pluran, pluran derivatives, polyacrylamide, polyvinyl alcohol., polyvinylpyrrolidone, etc.

A suitable dry. thickness of the detecting layer or water-absorbent layer ranges from about 1 to about 100 μm, and preferably from about 3 to about 30 μm.

An adhesive layer may be formed for adhering the spreading layer on the detecting layer or water-absorbent layer either directly or via a light-shielding layer, a filter layer, a reactive reagent layer, etc. The adhesive layer preferably comprises a hydrophilic polymer which becomes adhesive to the spreading layer when wetted or swollen with water. Such a hydrophilic polymer includes those enumerated for the water-absorbent layer or detecting layer. Preferred of these are gelatin, gelatin derivatives, polyacrylamide, and the like. The adhesive layer usually has a dry thickness of from about 0.5 to about 20 μm, and preferably, from about 1 to about 10 μm. The adhesive layer may be provided not only on the detecting layer or water-absorbent layer, but also between any other adjacent layers, e.g., between a reactive reagent layer with its adjacent layer, for ensuring adhesion therebetween. The adhesive layer can be formed by coating an aqueous solution-containing the aforesaid hydrophilic polymer and, if desired, a surface active agent, etc., on a detecting layer, a reactive reagent layer, etc. by a well-known coating technique.

The reactive reagent layer of the dry analytical element according to the present invention comprises a reactive reagent which produces detectable component, such as a substance forming or changing color, fluorescent substance, etc. by a reaction with a product formed by an enzyme reaction with substrate and may contain, if necessary, a hydrophilic polymer, a buffer agent, light-shielding fine particles (either reflective or absorbable), and the like.

The hydrophilic polymer which can be used in the reactive reagent layer includes starch, cellulose, agarose, gelatin and derivatives thereof (e.g., hydroxymethylated derivatives, hydroxypropylated derivatives, etc.), acrylamide polymers, copolymers of acrylamide and various vinyl monomers, polyvinyl alcohol, copolymers of vinylpyrrolidone and various vinyl monomers, acrylate polymers, copolymers of acrylates and various vinyl monomers, and the like. Of these hydrophilic polymers, polyvinyl alcohol, vinylpyrrolidone polymers, acrylamide polymers and cellulose derivatives are preferred.

The buffer agents to be used in the reactive reagent layer are conventional and include carbonates, borates, phosphates, Good's buffer agents, etc. Selection of the buffer agent to be used can be made by reference to literatures, e.g., Takeichi Horio, et al., *Tanpakushitsu Koso no Kisojikkenho*, Nankodo (1981).

The light-shielding layer is preferably a water permeable layer comprising a hydrophilic polymer as a binder having dispersed therein; light-reflective fine particles. When a detectable change produced in the detecting layer, such as, color change, color development, etc., is measured by reflective colorimetry from the side of the support having light transmission properties, the light-shielding layer containing reflective fine particles functions to shield the color of an aqueous liquid spot supplied and developed in the spreading layer, particularly a red color of hemoglobin in the case of analyzing whole blood. It also functions as a light-reflecting layer or a background layer.

Examples of the light-reflective fine particles which can be used in the light-shielding layer are pigment fine particles, such as, titanium dioxide fine particles (rutile-type, anatase-type or brookite-type fine crystal grains having a grain size of from about 0.1 to about 1.2 $\mu$m), barium sulfate fine particles, aluminum fine particles, etc., with titanium dioxide fine particles and barium sulfate fine particles being preferred.

The above-described light-schielding fine particles may also be used in the reactive reagent layer or the spreading layer.

The hydrophilic polymer to be used as a binder in the light-shielding layer includes those enumerated for the detecting layer and, in addition, weakly hydrophilic regenerated cellulose, cellulose acetate, and the like. Preferred among them are gelatin, gelatin derivatives, and polyacrylamide. Of these, gelatin and gelatin derivatives may contain known gelatin hardeners.

The above-described light-shielding layer can be formed by coating an aqueous dispersion comprising the light-shielding fine particles and the hydrophilic polymer on the detecting layer, the reactive reagent layer, or the like in a usual manner, followed by drying.

The water non-absorbent fibers which can be used in &he spreading layer according to the present invention include polyester fibers, such as; polyethylene terephthalate, polyamide fibers, such as, nylon, acrylic fibers, polyethylene fibers, polypropylene fibers, cellulose acetate fibers, and mixtures thereof. The spreading layer may be made of any of non-woven fabric, woven fabric and knitted fabric composed of these fibers. The fabric to be used is preferably subjected to dewaxing, such as, washing with water, to substantially remove fats and oils adhered during production of yarns or woven or knitted fabric. According to the present invention, a hydrophilic polymer selected from the polymers containing the repeating unit of formula (I) or (II) and the cellulose derivatives is incorporated into voids of the fibrous spreading layer in the form of a gel.

The dry analytical element for assaying enzymatic activities according to the present invention exhibits high analytical sensitivity and reproducibility. In particular, these effects are pronouncedly produced in analytical elements having a spreading layer containing a self-developable substrate capable of releasing a colored substance upon enzymatic reaction, such as, a GGT ($\gamma$-glutamyl transferase); activity assaying element using $\gamma$-glutamyl-p-nitroanilide, an amylase activity assaying element using a p-nitrophenyl oligosaccharide, saccharide, an ALP (alanine amino phosphatase); activity assaying element using p-nitrophenyl phosphate, and the like. The analytical element of the present invention is also useful in analysis systems using other substrates, such as assay of ALT, AST, LDH, etc., using alanine, asparatic acid, $\alpha$-ketoglutaric acid, lactic acid, etc., as a substrate.

The present invention is now illustrated in greater detail with reference to the following examples, but it should be understood that the present invention is not deemed to be limited thereto. In these examples, all the percents are by weight unless otherwise indicated.

EXAMPLE 1

An aqueous solution having Formulation (a–i) shown below was coated on a 180 $\mu$m thick colorless, transparent, and smooth polyethylene terephthalate film having a gelatin subbing layer to a dry thickness of 7 $\mu$m, followed by drying to form a detecting layer.

| Formulation (a-i): | |
|---|---|
| Gelatin | 300 g |
| Surfactant 10 G (surface active agent produced by Olin Corp.; p-nonylphenoxy polyglycidol; polymerization degree, about 10) | 5 g |
| 15% latex solution of poly-co-(styrene-N—methyl morpholinium methyl styrene-divinylbenzene) (55:43:2 by mol) | 280 g |
| Water | 2150 g |
| Dilute sodium hydroxide aqueous solution to adjust | pH = 7.0 |

An aqueous solution having Formulation (b–i) shown below was then coated on the thus formed gelatin layer to a dry thickness of 5 $\mu$m and dried to form a reactive reagent layer.

| Formultion (b-i): | |
| --- | --- |
| Gelatin | 200 g |
| Surfactant 10 G | 5 g |
| α-Glucosidase | 3500,000 IU |
| Water | 2600 g |
| Dilute sodium hydroxide aqueous solution to adjust | pH = 7.0 |

An aqueous solution having Formulation (c-i) shown below was further coated thereon to a dry thickness of 3 μm and dried to form a light-shielding layer.

| Formulation (c-i): | |
| --- | --- |
| Gelatin | 30 g |
| Surfactant 10 G | 4 g |
| Titanium oxide (anatase-type) | 20 g |
| Water | 950 g |
| Dilute sodium hydroxide aqueous solution to adjust | pH = 7.0 |

The light-shielding layer had a specular density (refer to *The Theory of the Photographic Process* (Third Edition), page 421, published by the Macmilian Company) of about 1.3.

After about 30 g/m² of water was uniformly supplied on the light-shielding layer to swell the layer, polyester knitted fabric (40 gauges) was laminated thereon under slight pressure, followed by drying. An aqueous solution having Formulation (d-i) shown below was uniformly applied on the fabric in an amount of 150 ml/m² and dried to remove the solvent to form a spreading layer. Thus, an integral multilayer analytical element for amylase assay was prepared.

| Formulation (d-i): | |
| --- | --- |
| p-Nitrophenyl α-D-maltopentaoside | 34 g |
| Water | 1600 g |
| Potassium phosphate | 60 g |
| Polyvinylpyrrolidone (average molecular weight: 100,000) | 140 g |
| Dilute sodium hydroxide aqueous solution to adjust | pH = 7.3 |

Ten microliters each of a commercially available control serum (Control Serum I) and a control serum with its amylase activity varied by addition of human saliva amylase (Control Serum II) were applied in a spot to the resulting analytical element. The element was allowed to stand at 37° C., and the reflective density of the element was measured every one minute between the period of from 3 to 6 minutes from the start of standing at a wavelength of 400 nm. The amylase concentration of Control Serums I and II were calculated from the change in reflective density using a previously prepared calibration curve. The results obtained are shown in Table 1.

TABLE 1

| Control Serum | Invention |
| --- | --- |
| I | 72 U/l |
| II | 238 U/l |

EXAMPLE 2

The same polyethylene terephthalate film as used in Example 1 was coated with an aqueous solution having Formulation (a-ii) and then with an aqueous solution having Formulation (b-ii) both shown below to a dry thickness of 10 μm and 3 μm, respectively, each followed by drying.

| Formulation (a-ii): | |
| --- | --- |
| Gelatin (alkali-processed deionized gelatin) | 100 g |
| Surfactant 10 G | 5 g |
| 1,2-Bis(vinylsulfonylacetamido)-ethane | 1.5 g |
| Water | 1000 g |
| Dilute sodium hydroxide aqueous solution to adjust | pH = 7.0 |

| Formulation (b-ii): | |
| --- | --- |
| Gelatin | 120 g |
| Surface active agent (nonylphenoxy polyglycidol) | 13 g |
| Water | 2600 g |
| Dilute sodium hydroxide aqueous solution to adjust | pH = 7.0 |

After the gelatin layer was swollen with 30 g/m² of a 0.4% aqueous solution of nonylphenoxy polyglycidol, a 230 μm thick polyester knitted fabric (36 gauges, 50 deniers) was laminated thereon under slight pressure, followed by drying.

Separately, four kinds of an aqueous solution (c-ii) were prepared by dispersing a solution of 22.8 g of γ-glutamyl p-nitroanilide in 10 ml of 2N hydrochloric acid and 10 ml of ethanol in a homogeneous solution having the following formulation and adjusting the pH to 8.3 with dilute hydrochloric acid.

| | |
| --- | --- |
| Tris(hydroxyethyl)aminomethane | 30.3 g |
| Glycylglycine | 6.5 g |
| Cetyltrimethylammonium bromide | 5 g |
| Surface active agent (nonylphenoxy polyglycidol) | 0.8 g |
| Water | 200 g |
| Polyacrylamide (viscosity: 2500 cps at 25° C.) | shown in Table 2 |

The resulting aqueous solution (c-ii) was uniformly coated on the fabric in an amount of 120 ml/m² and dried to prepare integral multi-layer analytical elements A, B, C, and D.

Each of the elements was cut in a 15×15 mm² square and fixed to a plastic mount described in Japanese Patent Application (OPI) No. 63452/62 to prepare a slide for GGT analysis. Ten microliters of 7% human serum albumin (HSA) containing 197, 382, or 889 IU/l of GGT were applied in spot to the resulting slide. The slide was allowed to stand in a closed container at 37° C., and the reflective optical density was measured at 41 nm after 2 and 5 minutes, and its change is shown in Table 2 below.

TABLE 2

| Sample | Amount of Polyacrylamide (g) | Change in Optical Density | | |
| --- | --- | --- | --- | --- |
| | | 197 IU/l | 382 IU/l | 889 IU/l |
| A | 5 | 0.073 | 0.113 | 0.154 |
| B | 10 | 0.088 | 0.139 | 0.198 |
| C | 15 | 0.105 | 0.147 | 0.209 |
| D | 0 | 0.052 | 0.072 | 0.102 |

Ten microliters of a 0.83 mM solution of Red No. 106 (food dye) was applied to the element, and the element was allowed to stand at 37° C. The spreading area on the spreading layer after 6 minutes standing was as shown in Table 3 below.

TABLE 3

| Sample | Developed Area (cm$^2$) |
|---|---|
| A | 1.50 |
| B | 1.34 |
| C | 1.18 |
| D | 1.90 |

EXAMPLE 3

The same procedure as in Example 2 was repeated to prepare a dry analytical element for assaying GGT except that the dried film produced from the solution (a-ii) was 15 μm in thickness, an amount of water in the solution (b-ii) was 2900 g, 2.5 g of polyacrylamide was incorporated into the solution (c-ii) instead of the surfactant and a solution (d-ii) having the following formulation was additionally coated in amount of 112 ml/m$^2$ after coating of the solution (c-ii).

| Formulation (d-ii) | |
|---|---|
| Hydroxyethylcellulose | 100 ml |
| TiO$_2$ | 5 g |

Ten microliters of 7% human serum albumin (HSA) containing 1900 IU/l of GGT were applied in spot to the resulting analytical element. The element was allowed to stand in a closed container at 37° C., and the reflective optical density was measured at 400 nm after 2 and 5 minutes from the start of the standing and the change between the two densities was found to be 0.223.

COMPARATIVE EXAMPLE

A dry analytical element for GGT assay was prepared in the same manner as in Example 3, except the the polyacrylamide was excluded from the formulation (c-ii).

Ten microliters of HSA containing 1900 IU/l of GGT were spotted on the resulting analytical element, and the system was kept at 37° C. in a closed container. The change of optical density when measured after 2 minutes and 5 minutes from the start of the standing was found to be 0.164.

EXAMPLE 4

A 180 μm thick transparent polyethylene terephthalate film was subjected to a treatment to render its surface hydrophilic. Onto the hydrophilic surface of the film was coated a coating solution having the following formulation and dried to form a color developing layer having a dry thickness of 10 μm.

| Formulation: | |
|---|---|
| Gelatin | 100 g |
| Water | 900 g |
| Nitroblue tetrazolium (3,3'-(3,3'-dimethoxy-4,4'-biphenylene)-bis[2(p-nitrophenyl)-5-phenyl-tetrazolium chloride]) | 6 g |

After the color developing layer was wetted with about 30 g/m$^2$ of water, knitted fabric composed of polyethylene terephthalate spun yarn (36 gauge, 50 denier) was applied thereon under pressure to form a spreading layer.

Onto the spreading layer was coated a coating solution having the following formulation to a coverage of 120 ml/m$^2$ and dried.

| Formulation: | |
|---|---|
| Water | 180 g |
| Imidazole | 4 g |
| Disodium creatine phosphate | 6 g |
| Adenosine diphosphate | 2.4 g |
| Adenosine 5'-phosphate | 4 g |
| Disodium ethylenediaminetetraacetate | 1.6 g |
| Magnesium acetate | 4 g |
| Glucose | 2 g |
| NAD | 2 g |
| N—Acetylcysteine | 0.6 g |
| Diadenosine pentaphosphate | 80 mg |
| Glucose-6-phosphate dehydrogenase | 30000 U |
| Hexokinase | 40000 U |
| Diaphorase | 30000 U |
| Ascorbic acid oxidase | 30000 U |
| Polyacrylamide (20% aqueous solution; average molecular weight: 37000) | 200 g |

Ten microliters of 7% HSA (37° C.) containing 0, 149, 383, 656 or 1560 IU/L of CPK (Creatine Kinase) were spotted on the spreading layer of the thus prepared analytical element, and the system was allowed to stand on a thermostatic plate at 37° C. while sufficiently preventing evaporation of water. The reflective optical densities were measured at 540 nm after 2 and 5 minutes, and the results obtained are shown in Table 4 below.

TABLE 4

| CPK Activity (IU/L) | Δ OD Optical Density | |
|---|---|---|
| | 2 mins | 5 mins |
| 0 | 0.515 | 0.584 |
| 149 | 0.599 | 0.757 |
| 383 | 0.657 | 0.932 |
| 656 | 0.811 | 1.237 |
| 1560 | 0.951 | 1.435 |

EXAMPLE 5

A 10 μm thick transparent polyethylene terephthalate film was subjected to a treatment to render its surface hydrophilic. Onto the hydrophilic surface of the film was coated a coating solution having the following formulation and dried to form a color developing layer having a dry thickness of about 10 μm.

| Formulation: | |
|---|---|
| Gelatin | 100 g |
| Water | 900 g |
| Surface active agent (octylphenyl polyglycidol) | 4 g |
| Nitroblue tetrazolium | 6 g |
| Bisvinylsulfone (2.7% solution in water:acetone = 1:1 by volume) | 74 g |
| | (pH = 6.5) |

After the color developing layer was wetted with about 30 g/m$^2$ of water, knitted fabric composed of polyethylene terephthalate spun yarn (36 gauge, 50 denier) was applied thereon under pressure to form a spreading layer.

Onto a spreading layer was coated a substrate solution having the following formulation to a coverage of 110 ml/m² and dried to prepare an integral multilayer analytical element for assaying CPK.

| Formulation: | |
| --- | --- |
| Water | 180 g |
| Imidazole | 4 g |
| Disodium creatine phosphate | 6 g |
| Adenosine diphosphate | 2.4 g |
| Adenosine 5'-phosphate | 4 g |
| Disodium ethylenediaminetetraacetate | 1.6 g |
| Magnesium acetate | 4 g |
| Glucose | 2 g |
| NAD | 2 g |
| N—Acetylcysteine | 0.6 g |
| Glucose-6-phosphate dehydrogenase | 14000 U |
| Hexokinase | 14000 U |
| Diaphorase | 14000 U |
| Surface active agent (TRITON-X-100; p-t-octylphenoxypolyethoxy ethanol; polymerization degree, about 10) | 3 g |
| Acrylamide/vinylpyrrolidone copolymer (50:50 by mol; 15% aqueous solution) | 100 ml/100 ml of the above formulation |

Ten microliters of 7% HSA containing 10 or 950 IU/L (37° C.) were spotted on the spreading layer, and the system was allowed to stand on a thermostatic plate at 37° C. while sufficiently preventing water evaporation. The reflective optical densities were measured at 510 nm after 2 and 5 minutes. The results obtained are shown in Table 5 below. The optical density of the analytical element before application of the CPK-containing solution was 0.43.

TABLE 5

| CPK Activity (IU/L) | Δ OD Optical Density | |
| --- | --- | --- |
| | 2 mins | 5 mins |
| 10 | 0.466 | 0.489 |
| 950 | 0.665 | 0.989 |

EXAMPLE 6

The same polyethylene terephthalate film as used in Example 1 was coated with an aqueous solution having Formulation (a-iii) and then with an aqueous solution having Formulation (b-iii) both shown below to a dry thickness of 10 μm and 3 μm, respectively, each followed by drying.

| Formulation (a-iii): | |
| --- | --- |
| Gelatin (alkali-processed deionized gelatin) | 100 g |
| Surfactant 10G | 5 g |
| 1,2-Bis(vinylsulfonylacetamido)-ethane | 1.5 g |
| Water | 1000 g |
| Dilute sodium hydroxide aqueous solution to adjust | pH = 7.0 |

| Formulation (b-iii): | |
| --- | --- |
| Gelatin | 120 g |
| Surface active agent (nonylphenoxy polyglycidol) | 13 g |
| Water | 2600 g |
| Dilute sodium hydroxide aqueous solution to adjust | pH = 7.0 |

After the gelatin layer was swollen with 30 g/m² of a 0.4% aqueous solution of nonylphenoxy polyglycidol, a 230 μm thick polyester knitted fabric (36 gauges, 50 deniers) as laminated thereon under slight pressure, followed by drying.

Separately, four kinds of an aqueous solution (c-iii) were prepared by dispersing a solution of 2.28 g of γ-glutamyl p-nitroanilide in 10 ml of 2N hydrochloric acid and 10 ml of ethanol in a homogeneous solution having the following formulation and adjusting the pH to 8.3 with dilute hydrocholoric acid.

| Formulation (c-iii) | |
| --- | --- |
| Tris(hydroxyethyl)aminomethane | 30.3 g |
| Glycylglycine | 6.5 g |
| Cetyltrimethylammonium bromide | 5 g |
| Surface active agent (nonylphenoxy polyglycidol) | 0.8 g |
| Water | 200 g |
| Hydroxypropyl-methyl cellulose | shown in Table 4 |

The resulting aqueous solution (c-iii) was uniformly coated on the fabric in an amount of 100 ml/m² and dried to prepare integral multi-layer analytical elements E, F, G, and H for assaying GGT activity.

A slide for GGT analysis was prepared using each of the analytical element E to H in the same manner as in Example 2.

Ten microliters of 7% HSA containing 172 or 1110 IU/l of GGT were applied in spot to the resulting slide. The slide was allowed to stand in a closed container at 37° C., and the reflective optical density was measured at 640 nm after 2 and 5 minutes, and its change is shown in Table 6-1 below.

TABLE 6-1

| | Amount of Hydroxy-propyl-Methyl Cellulose | Change in Optical Density | |
| --- | --- | --- | --- |
| Sample | (g) | 172 IU/l | 1110 IU/l |
| E | 0 | 0.050 | 0.164 |
| F | 2 | 0.065 | 0.184 |
| G | 4 | 0.070 | 0.189 |
| H | 6 | 0.074 | 0.193 |

The developed area on each of the GGT assaying elements was measured in the same manner as in Example 2, and the results obtained are shown in Table 6.2 below.

TABLE 6-2

| Sample | Developed Area (cm²) |
| --- | --- |
| E | 2.30 |
| F | 1.61 |
| G | 1.27 |
| H | 1.10 |

While the invention has been described in detail and with reference to specific embodiments thereof, it will be apparent to one skilled in the art that various changes and modifications can be made therein without departing from the spirit and scope thereof.

What is claimed:

1. A dry analytical element for assaying an enzyme activity in a liquid, which comprises a support having provided thereon at least a porous liquid-spreading layer composed of water non-absorbent fibers, wherein said porous liquid-spreading layer contains a substrate for an enzyme to be assayed and at least one water soluble hydrophilic polymer in an amount effective to decrease the spreading area of said porous liquid-spreading layer by at least 20%, wherein said hydrophilic polymer is selected from the group consisting of a polymer comprising a repeating unit represented by formula (I)

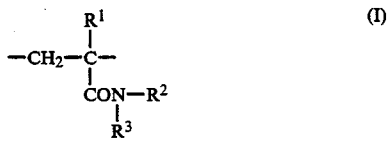

wherein $R^1$ represent a hydrogen atom or a lower alkyl group; and $R^2$ and $R^3$ each represents a hydrogen atom, a substituted or unsubstituted aliphatic hydrocarbon residue; a substituted or unsubstituted aromatic hydrocarbon residue, or a substituted or unsubstituted heterocyclic group, or $R^2$ and $R^3$ taken together form a ring.

2. A dry analytical element for assaying an enzyme activity in a liquid, which comprises a support having provided thereon at least a porous liquid-spreading layer composed of water non-absorbent fibers, wherein said porous liquid-spreading layer contains a substrate for an enzyme to be assayed and at least one water soluble hydrophilic polymer in an amount effective to decrease the spreading area of said porous liquid-spreading layer by at least 20%, wherein said hydrophilic polymer is a polymer comprising a repeating unit represented by formula (II)

wherein $R^4$ represents a hydrogen atom or a lower alkyl group; and Q represents:

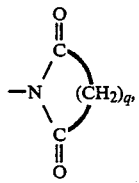

wherein q represents an integer of from 2 to 4, $-NR^5-CO-R^6$, wherein $R^5$ represents an alkyl group having from 1 to 4 carbon atoms, and $R^6$ represents a hydrogen atom or an alkyl group having from 1 to 4 carbon atoms; or

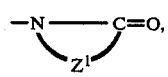

wherein $Z^1$ represents an atomic group forming a lactam ring, an oxazolidone ring or a pyridone ring.

3. The dry analytical element of claim 2, wherein $R^1$ represents a hydrogen atom or a methyl group; and $R^2$ and $R^3$ each represents a hydrogen atom, a methyl group, an ethyl group, a benzyl group, a hydroxyethyl group, a cyclohexyl group, a phenyl group, a piperidino group or a morpholino group, with the total number of carbon atoms in $R^2$ and $R^3$ being up to 12.

4. The dry analytical element of claim 2, wherein $R^4$ is a hydrogen atom; and Q represents:

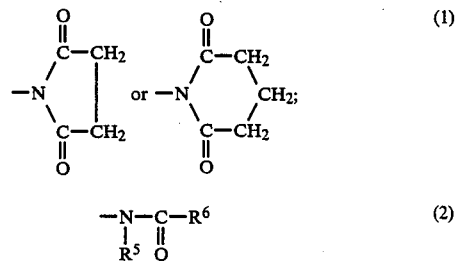

$$-\underset{R^5}{\underset{|}{N}}-\underset{O}{\overset{\|}{C}}-R^6 \quad (2)$$

wherein $R^5$ represents a methyl group or an ethyl group, and $R^6$ represents a hydrogen atom, a methyl group or an ethyl group; or

wherein $Z^1$ represents an atomic group forming a 5- or 6-membered lactam ring or an oxazolidone ring.

5. The dry analytical element of claim 4, wherein Q repressents a pyrrolidone residual group or an oxazolidone residual group.

6. The dry analytical element of claim 1, wherein said polymer comprising the repeating unit of formula (I) contains at least 20 mol % of said repeating unit of formula (I).

7. The dry analytical element of claim 2, wherein said polymer comprising the repeating unit of formula (I) or (II) is present in an amount of from 2 g to 15 g per m² of the liquid-spreading layer.

8. The dry analytical element of claim 1 wherein said polymer comprising the repeating unit of formula (I) contains at least 50 mol % of said repeating unit of formula (I).

9. The dry analytical element of claim 1 wherein said polymer comprising the repeating unit of formula (I) is present in an amount of from 2 g to 15 g per m² of the liquid-developing layer.

10. The dry analytical element of claim 2 wherein said polymer comprising the repeating unit of formula (II) contains at least 20 mol % of said repeating unit of formula (II).

11. The dry analytical element of claim 2 wherein said polymer comprising the repeating unit of formula (II) contains at least 50 mol % of said repeating unit of formula (II).

* * * * *